United States Patent [19]

Schneider et al.

[11] Patent Number: 4,529,815
[45] Date of Patent: Jul. 16, 1985

[54] PREPARATION OF 4-PENTENOATES

[75] Inventors: Heinz-Walter Schneider, Ludwigshafen; Rudolf Kummer, Frankenthal, both of Fed. Rep. of Germany

[73] Assignee: BASF Aktiengesellschaft, Fed. Rep. of Germany

[21] Appl. No.: 608,459

[22] Filed: May 9, 1984

[30] Foreign Application Priority Data

May 11, 1983 [DE] Fed. Rep. of Germany ....... 3317163

[51] Int. Cl.$^3$ ............................................ C07C 67/333
[52] U.S. Cl. .................................................. 560/205
[58] Field of Search ........................... 560/205; 502/74

[56] References Cited

U.S. PATENT DOCUMENTS

| | | | |
|---|---|---|---|
| 3,013,066 | 12/1961 | Alderson | 560/205 |
| 3,403,108 | 9/1968 | Leffin et al. | 560/205 |
| 3,450,730 | 6/1969 | Scheben et al. | 560/205 |
| 3,966,799 | 6/1976 | Hall et al. | 560/205 |
| 4,332,966 | 6/1982 | Isogai et al. | 560/206 |

OTHER PUBLICATIONS

Bull. of the Chem. Soc. of Japan, Band 46, S.528 Tetrahedron, vol. 28, S. 5769–5777 (1972).

*Primary Examiner*—James H. Reamer
*Assistant Examiner*—L. Hendriksen
*Attorney, Agent, or Firm*—Keil & Weinkauf

[57] ABSTRACT

4-Pentenoates are prepared by isomerization of isomeric pentenoates in the presence of a catalyst, by a process in which isomeric pentenoates are treated at elevated temperatures with an acidic ion exchanger or acidic zeolite which contains a noble metal of group eight of the periodic table, and the 4-pentenoate is distilled off from the reaction mixture.

7 Claims, No Drawings

PREPARATION OF 4-PENTENOATES

In the preparation of pentenoates by reacting butadiene with carbon monoxide and an alcohol in the presence of a metal carbonyl catalyst, as described in, for example, German Laid-Open Application DOS No. 3,040,432, substantial amounts of isomeric pentenoates are obtained. However, for further reactions, for example for the preparation of δ-formylvalerates by hydroformylation of pentenoates, 4-pentenoates are the preferred starting compounds. Attempts have therefore been made to obtain 4-pentenoates by isomerizing isomeric pentenoates. However, as disclosed in Bull. Chem. Soc. Japan 46, page 528, isomerization of methyl 3-pentenoate in the presence of a cobalt carbonyl gives predominantly methyl 2-pentenoate. Although in another procedure, described in Tetrahedron 28 (1972), 5769–77, the isomer equilibrium can be shifted in the presence of a complex of rhodium triphenylphosphine with tin chloride so that 4-pentenoates are obtained, the catalysts used in the said procedure become inactive in the course of a few hours.

When thermodynamic equilibrium is reached in the isomerization of the pentenoate, five isomers, ie. the 4-pentenoate, the cis- and trans-3-pentenoates and the cis- and trans-2-pentenoates, are present, the equilibrium being shifted strongly toward the trans-2-pentenoate, and less than 3% of the 4-pentenoate being obtained.

It is an object of the present invention to provide a process for the preparation of 4-pentenoates from isomeric pentenoates, in which the catalysts retain their activity over a prolonged period, and furthermore the linear shift of the double bond is preferentially towards the formation of the 4-pentenoate and very little of the cis-2-pentenoate, which is difficult to separate off, is formed.

We have found that this object is achieved by a process for the preparation of 4-pentenoates by isomerization of isomeric pentenoates in the presence of catalysts, wherein pentenoates are treated at elevated temperatures with an acidic ion exchanger or acidic zeolite which contains a noble metal of group 8 of the periodic table, and the 4-pentenoate is distilled off from the reaction mixture.

The novel process has the advantages that the catalysts used have a long life, and in particular that the linear shift of the double bond is preferentially toward formation of the 4-pentenoate, the concentration of the latter being substantially above the thermodynamic equilibrium concentration.

Advantageous starting materials are isomeric pentenoates, for example 2- or 3-pentenoates, which are derived from alcohols of not more than 12 carbon atoms. Isomeric alkyl pentenoates derived from, in particular, alcohols of not more than 4 carbon atoms are particularly preferably used. Examples of suitable 3-pentenoates are methyl 3-pentenoate, ethyl 3-pentenoate, propyl 3-pentenoate, butyl 3-pentenoate, methyl 2-pentenoate, ethyl 2-pentenoate and propyl 2-pentenoate.

The catalysts used are acidic ion exchangers or acidic zeolites, strongly acidic ion exchangers, eg. crosslinked polystyrenes containing acidic groups, in particular sulfonic acid groups, being preferably used. Styrene/divinylbenzene copolymers containing sulfonic acid groups have proven particularly useful, while preferred acidic zeolites are A, X and Y zeolites in the H, ie. acidic, form.

The acidic ion exchangers and acidic zeolites contain noble metals of group 8 of the periodic table, palladium, ruthenium and rhodium, in particular palladium, being preferred. The metal content is preferably from 0.01 to 1% by weight. The catalysts can be used as a fixed bed or in suspension.

The residence time of the isomeric pentenoates over the catalyst depends on the catalytic activity and the isomerization rate, and is as a rule from 0.01 to 1 hour. Advantageously, from 0.01 to 0.3 kg of catalyst is used per kg of isomeric pentenoates.

The temperature depends essentially on the boiling point of the 4-pentenoate being prepared, and is advantageously from 100° to 150° C. Where acidic ion exchangers based on polystyrene are used, temperatures from 110° to 140° C. have proven useful. As a rule, the isomerization is carried out under atmospheric pressure, but reduced pressure or slightly superatmospheric pressure, eg. not more than 3 bar, can also be used, depending on the type of ester used.

After a sufficient amount of the 4-pentenoate has formed, it is distilled off from the isomer mixture, and the remaining isomer mixture is again brought into contact with the catalyst. In this way, the 4-pentenoate is distilled off continuously from the isomerization mixture.

The treatment with the catalyst can be carried out batchwise, but a continuous procedure is preferred. The remaining isomer mixture is advantageously recycled to the isomerization.

4-Pentenoates are useful for the preparation of δ-formylvalerates, which are precursors for the preparation of ε-caprolactam, hexanediol and adipic acid.

The Examples which follow illustrate the process.

EXAMPLES

Example 1

In a glass flask, 100 g of a mixture of 70% by weight of methyl trans-3-pentenoate and 30% by weight of methyl cis-2-pentenoate, as obtained in the carbonylation of 1,3-butadiene, are stirred, at 135° C., with 10 g of a catalyst of the Y zeolite type, laden with 0.5% by weight of palladium. After a reaction time of 6 minutes, the resulting reaction mixture is composed of 8% by weight of 4-pentenoate, 0.1% by weight of the cis-3-pentenoate, 64.3% by weight of the trans-3-pentenoate, 27.4% by weight of the cis-2-pentenoate and 0.2% by weight of the trans-2-pentenoate.

The catalyst productivity is 1600 g per g of Pd per hour, based on methyl 4-pentenoate.

The catalyst is separated off, and the reaction mixture is then distilled in a column (number of separation stages 100, reflux ratio 50). 8.2 g of 95% pure methyl 4-pentenoate are taken off at a top temperature of 126° C. The bottom product (91.8 g) is supplemented with fresh pentenoate mixture having the composition stated at the outset, the amount added corresponding to the amount distilled off (8.2 g), and is used again for the isomerization.

Example 2

The procedure is carried out similarly to that described in Example 1, except that an acidic ion exchanger consisting of crosslinked polystyrene and laden with 0.2% of palladium is used. After a reaction time of 18 minutes, the resulting reaction mixture contains 8.0% by weight of the 4-pentenoate.

The catalyst productivity is 1330 g per g of Pd per hour, based on the 4-pentenoate.

Example 3

The procedure is carried out similarly to that described in Example 1, except that an acidic ion exchanger laden with 0.7% of rhodium is used. After a reaction time of 25 minutes, the resulting reaction mixture contains 8% by weight of the 4-pentenoate.

The catalyst productivity is 271 g per g of Rh per hour, based on the 4-pentenoate.

Example 4

The procedure is carried out similarly to that described in Example 1, except that an acidic ion exchanger laden with 0.4% of ruthenium is used. After 96 minutes, the resulting reaction mixture contains 8% of the 4-pentenoate.

The catalyst productivity is 125 g per g of Ru per hour, based on the 4-pentenoate.

We claim:

1. A process for the preparation of a 4-pentenoate by isomerization of pentenoates, wherein pentenoates are treated at elevated temperatures with an acidic ion exchanger or acidic zeolite which contains palladium, ruthenium or rhodium, and the 4-pentenoate is distilled off from the reaction mixture.

2. The process of claim 1, wherein the acidic ion exchanger or acidic zeolite contains from 0.01 to 1% by weight of a noble metal of group eight of the periodic table.

3. The process of claim 1, wherein the temperature is from 100° to 150° C.

4. The process of claim 1, wherein the residence time over the catalyst is from 0.01 to 1 hour.

5. The process of claim 1, wherein the acidic ion exchanger or acidic zeolite contains palladium.

6. The process of claim 1, wherein the acidic ion exchanger or acidic zeolite contains ruthenium.

7. The process of claim 1, wherein the acidic ion exchanger or acidic zeolite contains rhodium.

* * * * *